(12) United States Patent
Johnson et al.

(10) Patent No.: US 9,170,059 B2
(45) Date of Patent: Oct. 27, 2015

(54) HEAT TRANSFER PAD HAVING LOCALIZED TREATMENT ZONES

(75) Inventors: Michael G. Johnson, Escondido, CA (US); Stefanie L. Mah, El Cajon, CA (US); James M. Fout, Oceanside, CA (US); Christian L. Hansen, Vista, CA (US)

(73) Assignee: Breg, Inc., Carlsbad, CA (US)

( * ) Notice: Subject to any disclaimer, the term of this patent is extended or adjusted under 35 U.S.C. 154(b) by 703 days.

(21) Appl. No.: 13/007,598

(22) Filed: Jan. 14, 2011

(65) Prior Publication Data

US 2012/0185021 A1    Jul. 19, 2012

(51) Int. Cl.
 A61F 7/00    (2006.01)
 F28F 3/12    (2006.01)
 A61F 7/02    (2006.01)

(52) U.S. Cl.
 CPC ... *F28F 3/12* (2013.01); *A61F 7/00* (2013.01); *A61F 7/02* (2013.01); *A61F 2007/004* (2013.01); *A61F 2007/0054* (2013.01); *A61F 2007/0228* (2013.01)

(58) Field of Classification Search
 USPC ............ 607/96, 104, 108–112; 165/46; 606/20–26; 62/530; 602/2
 See application file for complete search history.

(56) References Cited

U.S. PATENT DOCUMENTS

| | | |
|---|---|---|
| 2,726,658 A | 12/1955 | Chessey |
| 3,086,395 A | 4/1963 | York |
| 3,548,819 A | 12/1970 | Davis et al. |
| 3,683,902 A | 8/1972 | Artemenko et al. |
| 3,901,225 A | 8/1975 | Sconce |
| 4,098,279 A | 7/1978 | Golden |
| 4,706,658 A | 11/1987 | Cronin |
| 4,718,429 A * | 1/1988 | Smidt .......................... 607/104 |
| 4,962,761 A | 10/1990 | Golden |
| 5,035,146 A | 7/1991 | Chien |
| 5,086,771 A | 2/1992 | Molloy |
| 5,184,613 A | 2/1993 | Mintz |
| 5,190,032 A | 3/1993 | Zacoi |
| 5,241,951 A | 9/1993 | Mason et al. |
| D345,609 S | 3/1994 | Mason et al. |
| D348,106 S | 6/1994 | Mason et al. |
| 5,324,319 A | 6/1994 | Mason et al. |
| D348,518 S | 7/1994 | Mason et al. |
| 5,330,519 A | 7/1994 | Mason et al. |
| D351,472 S | 10/1994 | Mason et al. |
| 5,411,542 A * | 5/1995 | Jensen .......................... 607/104 |
| 5,417,720 A | 5/1995 | Mason et al. |
| 5,470,353 A | 11/1995 | Jensen |
| 5,507,792 A | 4/1996 | Mason et al. |
| 5,643,336 A | 7/1997 | Lopez-Claros |

(Continued)

*Primary Examiner* — Joseph Stoklosa
*Assistant Examiner* — Adam Avigan
(74) *Attorney, Agent, or Firm* — Rodney F. Brown

(57) ABSTRACT

A heat transfer pad includes a pad inlet port for feeding a heat transfer fluid to the pad, a pad outlet port for discharging the heat transfer fluid from the pad and a bladder having an internal flowpath for the heat transfer fluid which extends from the pad inlet port to the pad outlet port. The internal flowpath is divided into a first flow channel and a second flow channel through which first and second flow streams of the heat transfer fluid, respectively, flow between the pad inlet and outlet ports. A first flow restrictor is positioned downstream in the first flow channel and a second flow restrictor is correspondingly positioned downstream in the second flow channel and the flow restrictors are configured to create substantial back pressures in the first and second flow channels, respectively.

24 Claims, 8 Drawing Sheets

(56) References Cited

U.S. PATENT DOCUMENTS

| | | | |
|---|---|---|---|
| 5,662,695 A | 9/1997 | Mason et al. | |
| 5,683,439 A * | 11/1997 | Jensen | 607/104 |
| 5,735,890 A | 4/1998 | Kappel et al. | |
| 5,865,841 A | 2/1999 | Kolen et al. | |
| 5,980,561 A | 11/1999 | Kolen et al. | |
| 6,113,626 A | 9/2000 | Clifton et al. | |
| 6,117,164 A | 9/2000 | Gildersleeve et al. | |
| 6,176,869 B1 | 1/2001 | Mason et al. | |
| 6,197,045 B1 | 3/2001 | Carson | |
| 6,238,427 B1 * | 5/2001 | Matta | 607/104 |
| 6,500,200 B1 | 12/2002 | Kushnir | |
| 6,648,905 B2 * | 11/2003 | Hoglund et al. | 607/104 |
| 6,669,715 B2 | 12/2003 | Hoglund et al. | |
| 6,736,836 B2 * | 5/2004 | Montgomery | 607/104 |
| 7,001,417 B2 * | 2/2006 | Elkins | 607/104 |
| 7,066,949 B2 | 6/2006 | Gammons et al. | |
| 7,306,568 B2 | 12/2007 | Diana | |
| 7,377,935 B2 | 5/2008 | Schock et al. | |
| 7,621,945 B2 | 11/2009 | Lennox et al. | |
| 7,637,931 B2 | 12/2009 | Heaton | |
| 7,896,910 B2 | 3/2011 | Schirrmacher et al. | |
| 7,914,563 B2 | 3/2011 | Mason et al. | |
| 2007/0100404 A1 * | 5/2007 | Ko et al. | 607/104 |
| 2007/0118194 A1 | 5/2007 | Mason et al. | |
| 2008/0228248 A1 * | 9/2008 | Guyuron et al. | 607/108 |

\* cited by examiner

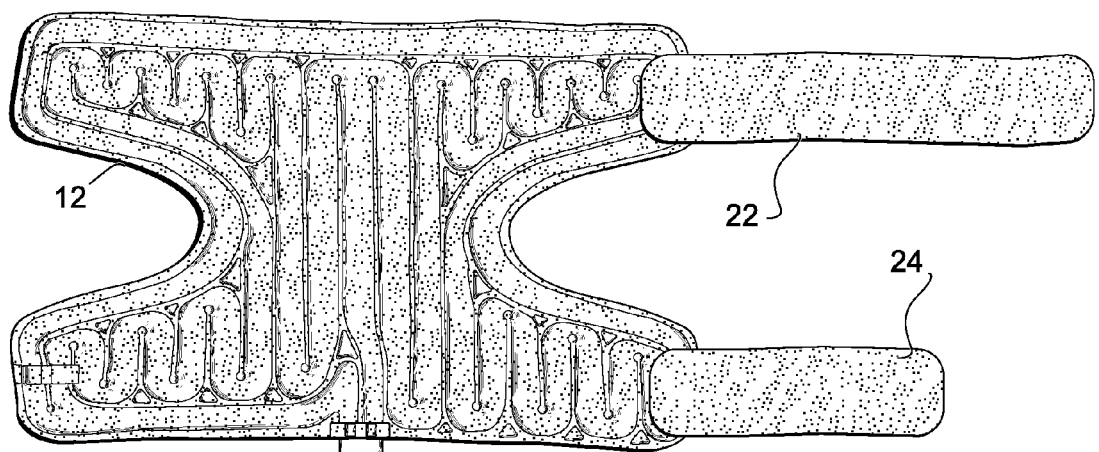
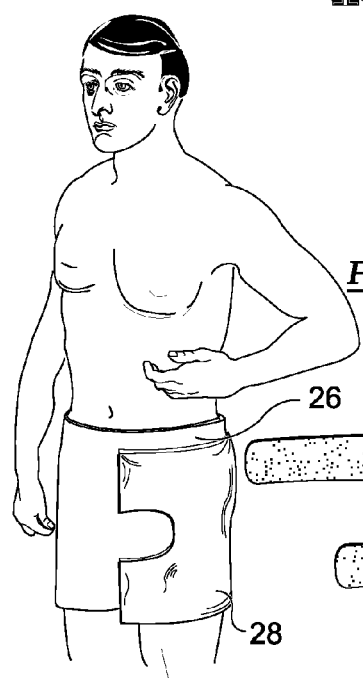
FIG. 10A
FIG. 9
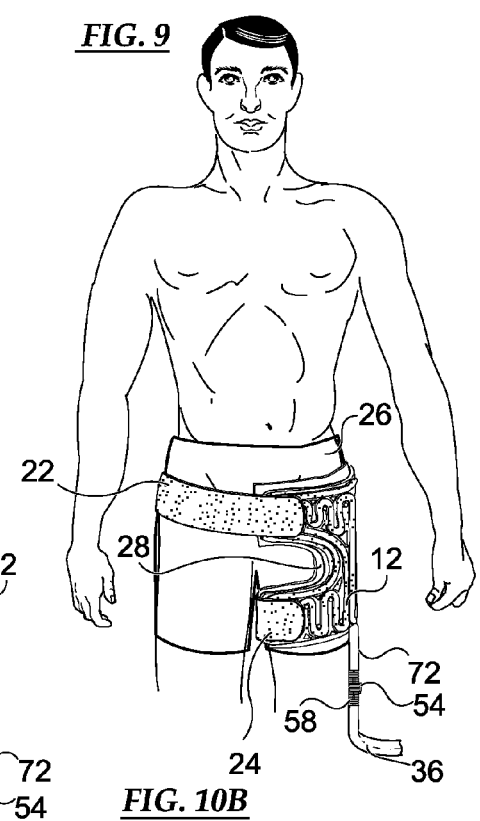
FIG. 10B

HEAT TRANSFER PAD HAVING LOCALIZED TREATMENT ZONES

TECHNICAL FIELD

The present invention relates generally to therapeutic treatment of bodily injuries and ailments by cooling or heating an affected region of the body of a patient, and more particularly, to a heat transfer pad having a non-ambient temperature heat transfer fluid circulated therethrough which is positioned on the affected region to cool or heat the region.

BACKGROUND OF THE INVENTION

Bodily injuries and ailments are commonly treated by applying a non-ambient temperature material to the affected region of the body. For example, a low temperature material, typically applied in the form of cold water, ice or a cold pack, may advantageously inhibit swelling in the region of the injury. A high temperature material, typically applied in the form of hot water, a hot pack or an active heating element, may advantageously reduce pain and promote healing. A number of splint devices are known in the art for applying non-ambient temperature materials to injured or otherwise ailing regions of the body as evidenced by U.S. Pat. No. 3,548,819 to Davis et al; U.S. Pat. No. 3,901,225 to Sconce; and U.S. Pat. No. 4,706,658 to Cronin. One disadvantage of such devices is that the low temperature materials become warmer as they remain in contact with the body and the body transfers heat to the low temperature materials. Conversely, high temperature materials become cooler as they transfer heat to the body. This disadvantage can be remedied by periodically replacing the non-ambient temperature materials. However, constant replenishment of these materials is cumbersome and inconvenient, and results in periodic treatment temperature fluctuations.

In response to this problem, a number of systems have been developed for continuously circulating a cooling fluid from a low temperature reservoir to a desired body location. Such systems are typified by U.S. Pat. No. 2,726,658 to Chessey; U.S. Pat. No. 3,683,902 to Artemenko et al; and U.S. Pat. No. 4,962,761 to Golden. These fluid circulation systems in general are relatively complex, rendering them costly to manufacture and maintain, as well as difficult to operate. Accordingly, the systems are not practical for widespread use.

U.S. Pat. No. 5,241,951 to Mason et al. incorporated herein by reference discloses a therapeutic treatment system which rectifies the shortcomings of the above-referenced fluid circulation systems. The therapeutic treatment system of U.S. Pat. No. 5,241,951 is relatively simple, rendering it less costly to manufacture and maintain and enabling greater ease of operation than the prior systems. The therapeutic treatment system of U.S. Pat. No. 5,241,951 is operated by circulating a non-ambient temperature heat transfer fluid through a heat transfer pad. Specific examples of heat transfer pads having utility in the therapeutic treatment system of U.S. Pat. No. 5,241,951 are disclosed in commonly-owned U.S. Pat. Nos. 5,417,720; 5,662,695; D.348,106 and D.345,609 all to Mason et al. and all of which are incorporated herein by reference.

The present invention recognizes the need for improved performance of the heat transfer pad in a non-ambient temperature therapy system such as those described above. Accordingly, it is generally an object of the present invention to provide a non-ambient temperature therapy system having a heat transfer pad exhibiting improved performance. This object and others are achieved in accordance with the invention described hereafter.

SUMMARY OF THE INVENTION

The present invention is a heat transfer pad including a pad inlet port for feeding a heat transfer fluid to the pad, a pad outlet port for discharging the heat transfer fluid from the pad and a bladder having an internal flowpath for the heat transfer fluid to flow therethrough. The internal flowpath extends from the pad inlet port to the pad outlet port and is divided into a first flow channel and a second flow channel, both of which are between the pad inlet and outlet ports. A first flow stream of the heat transfer fluid flows through the first channel at a first flow rate and a second flow stream of the heat transfer fluid flows through the second flow channel at a second flow rate. The first and second flow rates are preferably essentially equal to one another.

Each flow channel has a defined continuous containment width along its length which substantially prevents fluid communication between the first and second flow channels, thereby substantially preventing mixing of the first flow stream while in the first flow channel with the second flow stream while in the second flow channel. The defined continuous containment width of the first flow channel preferably substantially prevents back mixing of the first flow stream with itself within the first flow channel and the defined continuous containment width of the second flow channel likewise preferably substantially prevents back mixing of the second flow stream with itself within the second flow channel.

The first flow channel is preferably substantially undivided so that the first flow stream remains a substantially single undivided stream within the first flow channel and the second flow channel is similarly preferably substantially undivided so that the second flow stream remains a substantially single undivided stream within the second flow channel. The first and second flow channels are preferably positioned on substantially opposite sides of the heat transfer pad from one another and the first and second flow channels preferably have first and second tortuous portions, respectively, which are configured as substantially mirror images of one another on the opposite sides of the heat transfer pad. The first flow channel is preferably configured with a series of side-by-side switchback sections enabling counter-current flow from one switchback section to the next in series and the second flow channel is preferably similarly configured with a series of side-by-side switchback sections.

In accordance with one embodiment, the heat transfer pad further comprises an inlet chamber at the interface of the pad inlet port and the first and second flow channels. The first flow stream flows into the first flow channel from the inlet chamber via a first flow opening and the second flow stream flows into the second flow channel from the inlet chamber via a second flow opening. The first flow opening preferably has a width essentially equal to the defined continuous containment width of the first flow channel and the second flow opening preferably has a width essentially equal to the defined continuous containment width of the second flow channel.

In accordance with another embodiment, the heat transfer pad further comprises an outlet chamber at the interface of the pad outlet port and the first and second flow channels. The first flow stream flows from the first flow channel into the outlet chamber via a first partition terminus and the second flow stream flows from the second flow channel into the outlet chamber via a second partition terminus. A first flow restrictor is positioned in the first partition terminus and a second flow restrictor is positioned in the second partition terminus. The first and second flow restrictors are configured to create substantial back pressures in the first and second flow channels, respectively. In accordance with one alternative, the first and second flow restrictors are similarly configured as pin hole orifices to create the substantial back pressures in the first and second flow channels, respectively. In accordance with another alternative, the first and second flow restrictors are configured to create sufficient back pressures in the first and second flow channels, respectively, so that if the first or second flow channel is occluded upstream of the corresponding first or second flow restrictor, the first and second flow rates of the first and second flow streams remain essentially equal.

The present invention is alternately characterized as a heat transfer pad including a pad inlet port for feeding a heat transfer fluid to the pad, a pad outlet port for discharging the heat transfer fluid from the pad and a bladder having an internal flowpath for the heat transfer fluid to flow therethrough. The internal flowpath extends from the pad inlet port to the pad outlet port and is divided into a first flow channel and a second flow channel, both of which are between the pad inlet and outlet ports. A first flow stream of the heat transfer fluid flows through the first channel at a first flow rate and a second flow stream of the heat transfer fluid flows through the second flow channel at a second flow rate. In accordance with one embodiment, each flow channel has a defined continuous containment width along its length which substantially prevents fluid communication between the first and second flow channels, thereby substantially preventing mixing of the first flow stream while in the first flow channel with the second flow stream while in the second flow channel.

The pad has a first flow restrictor positioned downstream in the first flow channel and a second flow restrictor positioned downstream in the second flow channel. The first and second flow restrictors are configured to create substantial back pressures in the first and second flow channels, respectively. In accordance with another embodiment, the first and second flow restrictors are similarly configured as pin hole orifices to create the substantial back pressures in the first and second flow channels, respectively. In accordance with yet another embodiment, the first and second flow restrictors are configured to create sufficient back pressures in the first and second flow channels, respectively, so that if the first or second flow channel is occluded upstream of the corresponding first or second flow restrictor, the first and second flow rates of the first and second flow streams remain essentially equal.

The present invention is alternately characterized as a heat transfer pad including a pad inlet port for feeding a heat transfer fluid to the pad, a pad outlet port for discharging the heat transfer fluid from the pad and a bladder having an internal flowpath for the heat transfer fluid to flow therethrough. The internal flowpath extends from the pad inlet port to the pad outlet port and is divided into a first flow channel and a second flow channel, both of which are between the pad inlet and outlet ports. A first flow stream of the heat transfer fluid flows through the first channel at a first flow rate and a second flow stream of the heat transfer fluid flows through the second flow channel at a second flow rate. Each flow channel has a defined continuous containment width along its length which substantially prevents fluid communication between the first and second flow channels, thereby substantially preventing mixing of the first flow stream while in the first flow channel with the second flow stream while in the second flow channel.

The pad has an outlet chamber at the interface of the pad outlet port and the first and second flow channels. The first flow stream flows from the first flow channel into the outlet chamber via a first partition terminus and the second flow stream flows from the second flow channel into the outlet chamber via a second partition terminus. A first flow restrictor is positioned in the first partition terminus and a second flow restrictor is positioned in the second partition terminus. The first and second flow restrictors are configured to create substantial back pressures in the first and second flow channels, respectively.

In accordance with one embodiment, the heat transfer pad further comprises an inlet chamber at the interface of the pad inlet port and the first and second flow channels. The first flow stream flows into the first flow channel from the inlet chamber via a first flow opening and the second flow stream flows into the second flow channel from the inlet chamber via a second flow opening.

The present invention will be further understood from the drawings and the following detailed description.

BRIEF DESCRIPTION OF THE DRAWINGS

The accompanying drawings illustrate certain aspects of the present invention, but should not be viewed as by themselves limiting or defining the invention.

FIG. 9 is a rear view of the heat transfer pad of the present invention having retention straps removably attached thereto.

FIGS. 10A and 10B show operative mounting of the heat transfer pad of FIG. 9 on the hip of a patient.

Figure 1:
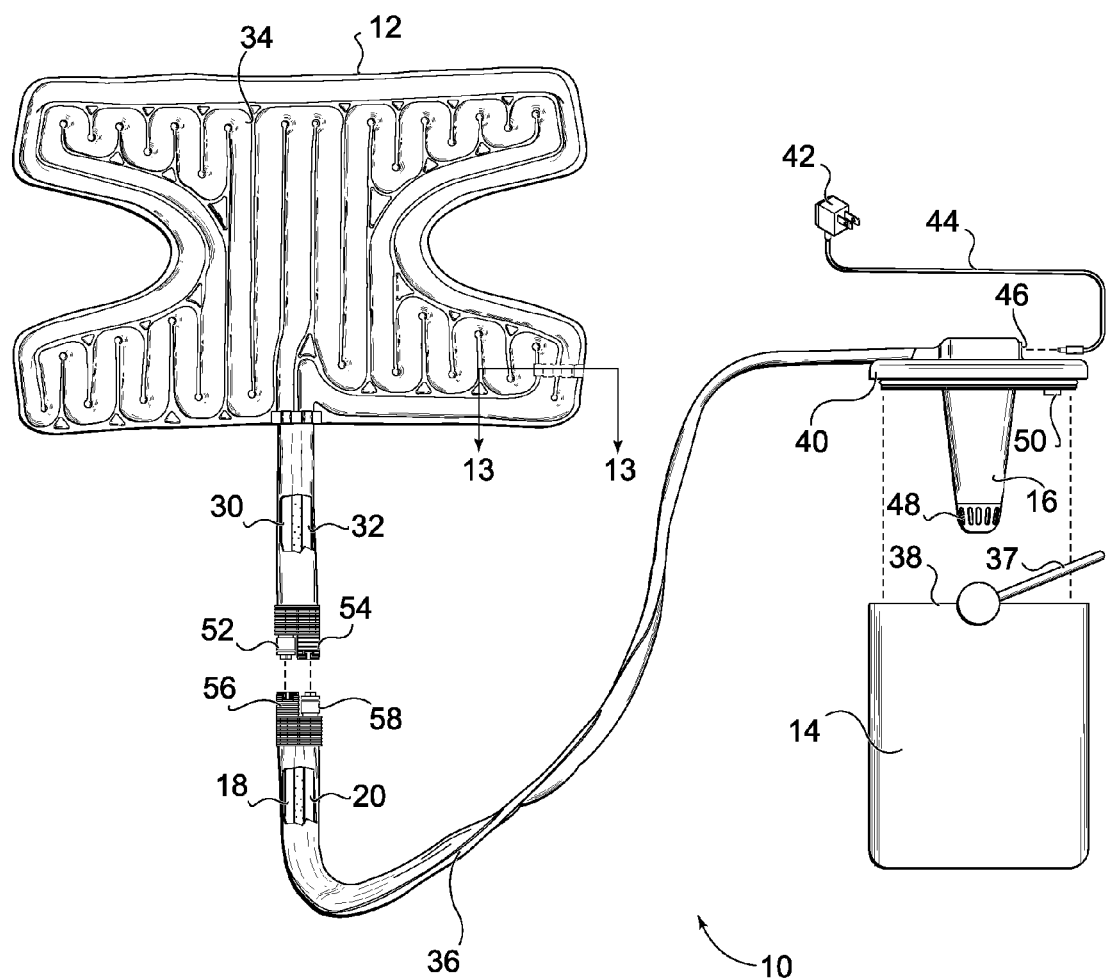
FIG. 1 is an exploded view of a non-ambient temperature therapy system which includes the heat transfer pad of the present invention.
Figure 2:
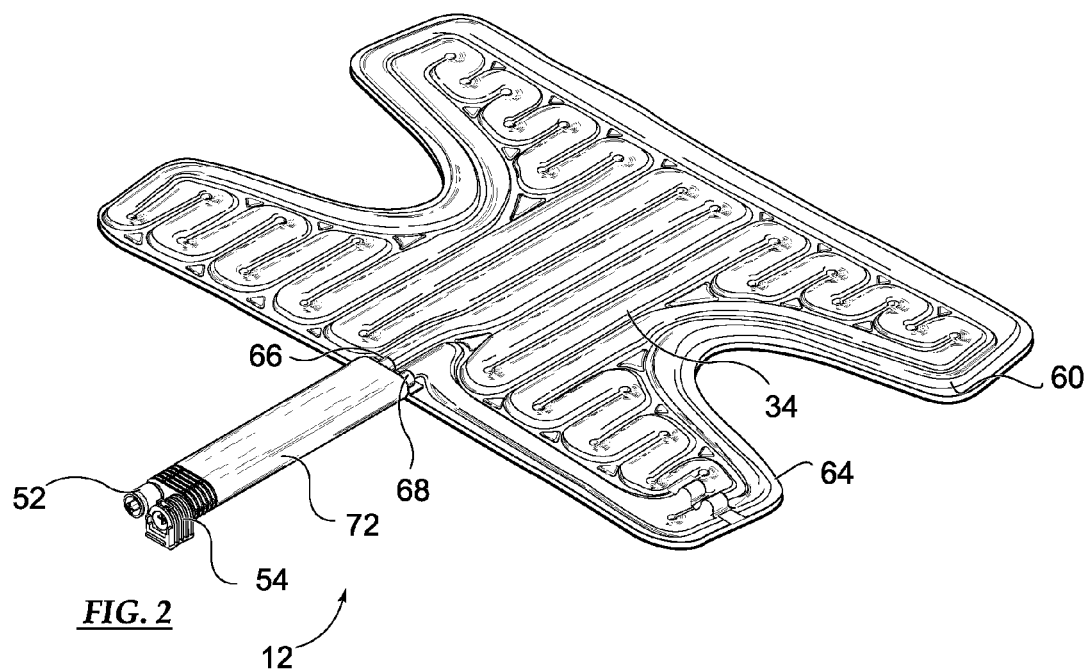
FIG. 2 is a front perspective view of the heat transfer pad of FIG. 1.
Figure 3:
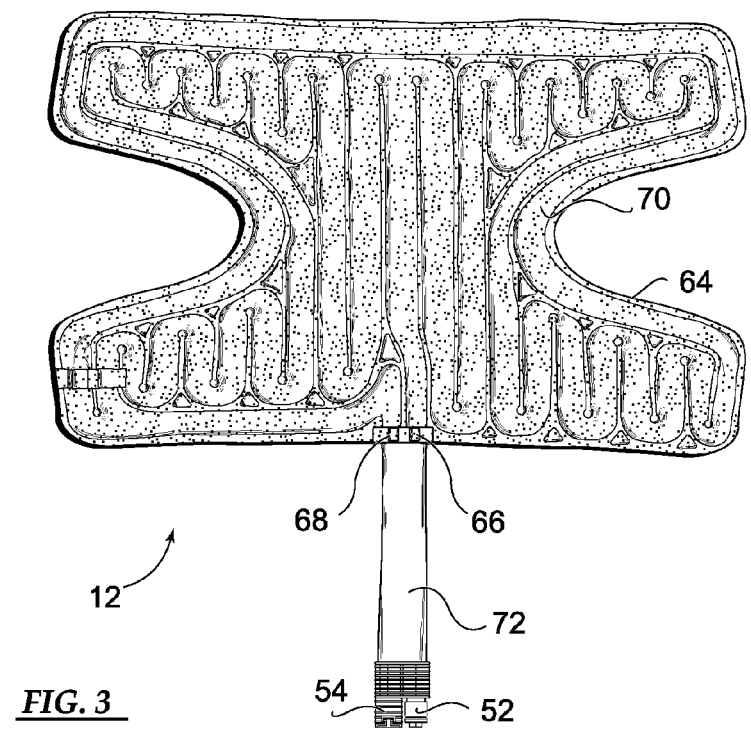
FIG. 3 is a rear view of the heat transfer pad of FIG. 1.
Figure 4:
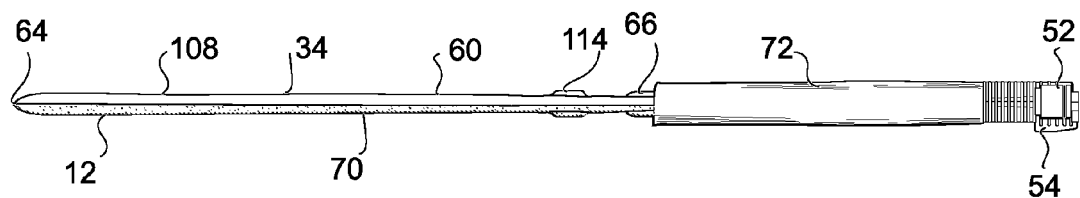
FIGS. 4 and 5 are elevation views of opposing sides of the heat transfer pad of FIG. 1.
Figure 5:
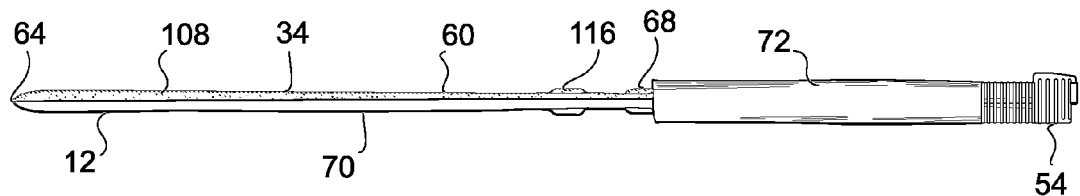
Figure 6:
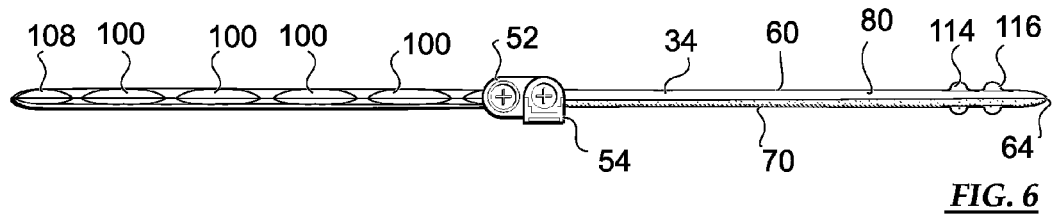
FIG. 6 is a bottom elevation view of the heat transfer pad of FIG. 1.
Figure 7:
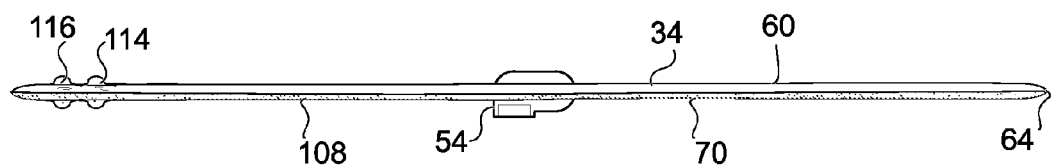
FIG. 7 is a top elevation view of the heat transfer pad of FIG. 1.
Figure 8:
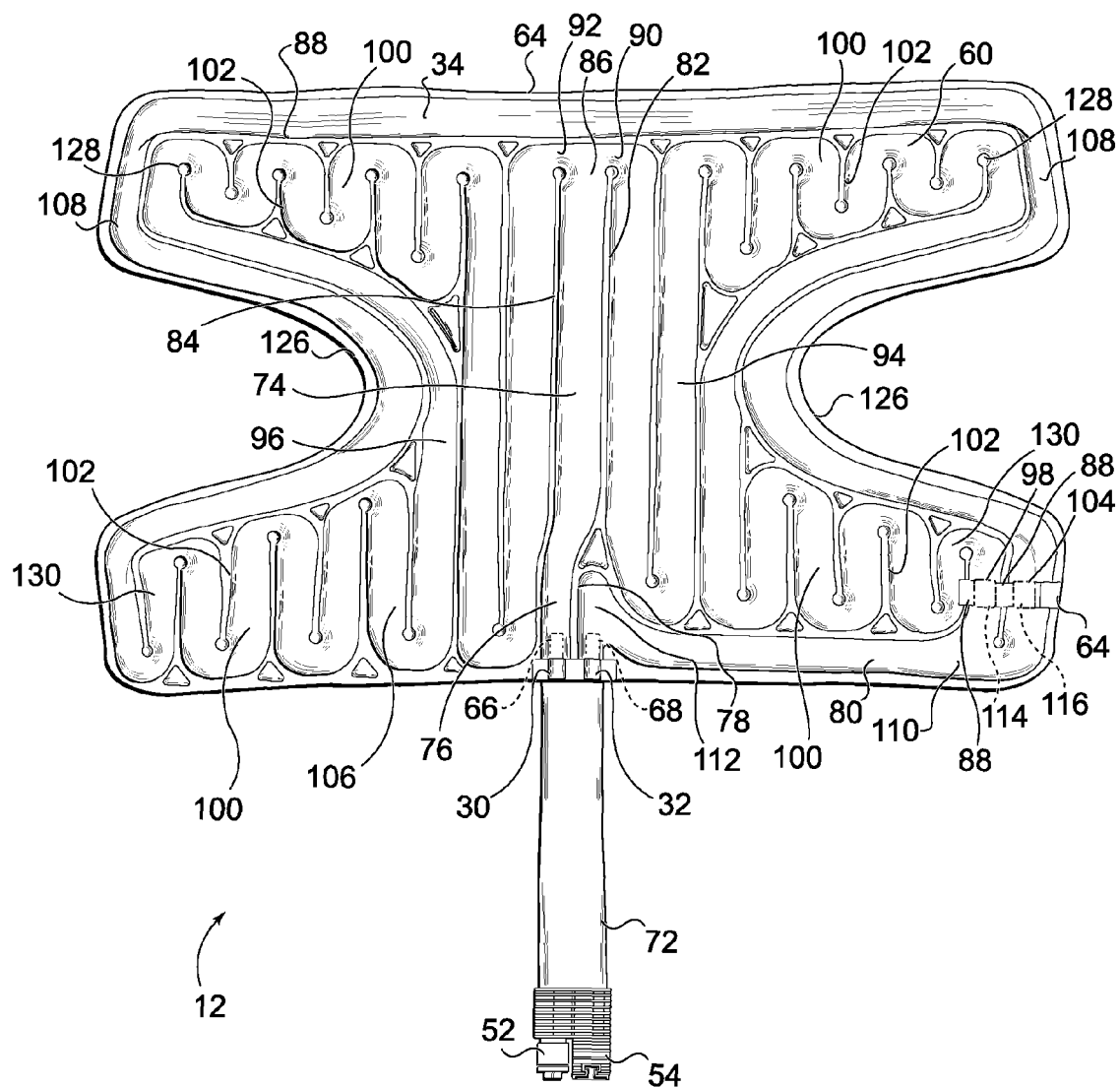
FIG. 8 is a front view of the heat transfer pad of FIG. 1.

Embodiments of the invention and prior art are illustrated by way of example and not by way of limitation in the above-recited figures of the drawings, wherein like reference characters indicate the same or similar elements. It should be noted that common references to "an embodiment", "one embodiment", "an alternate embodiment", "a preferred embodiment", or the like herein are not necessarily references to the same embodiment.

DESCRIPTION OF PREFERRED EMBODIMENTS

FIG. 1 shows an exemplary non-ambient temperature therapy system generally designated 10 in which a heat transfer pad of the present invention has utility. The system 10 comprises the heat transfer pad 12, through which a heat transfer fluid is circulated, and a reservoir 14, which is a source of fresh heat transfer fluid. The system further comprises a pump 16, a fresh fluid feed line 18 and a spent fluid return line 20 (shown in a partial cutaway) which enable continuous steady-state circulation of the heat transfer fluid from the reservoir 14, through the pad 12 and back to the reservoir 14 in a manner described in detail below.

The intended use of the system 10 is for administering non-ambient temperature therapy to a patient on whom the heat transfer pad 12 is mounted. Although the patient may use the system 10 to self-administer the therapy during individual sessions, the overall non-ambient temperature therapy program is typically under the direction of a health care practitioner. The term "non-ambient temperature" is used herein relative to the ambient body temperature of the patient. Accordingly, non-ambient temperature therapy is termed high temperature therapy when the temperature of fresh heat transfer fluid in the reservoir 14 is greater than the ambient body temperature of the patient. Conversely, non-ambient temperature therapy is termed low temperature therapy, or alternatively cold therapy, when the temperature of fresh heat transfer fluid in the reservoir 14 is less than the ambient body temperature of the patient.

The heat transfer pad 12 is preferably configured in correspondence with a desired treatment region of the body of a patient so that the pad 12 substantially covers and conforms to the contours of the treatment region, thereby enabling thorough and continuous contact between the pad 12 and the treatment region. It is further preferred that the geometry of the pad 12 is configured in a way that does not substantially block or unduly impair mobility of the patient on which the pad 12 is mounted.

The embodiment of the heat transfer pad 12 shown in the drawings and described in detail below is configured to be externally mounted on the hip of a patient which is the desired treatment region of the body. However, it is understood that the present invention is not limited to any one specific configuration of the heat transfer pad or any one specific treatment region of the body. The teaching set forth herein, as specifically illustrated by the heat transfer pad 12 for the hip, is generally applicable to heat transfer pads which are alternately configured for conformance to other desired treatment regions of the body such as the knee, ankle, shoulder, wrist, hand, back, head, etc. and such alternately configured heat transfer pads are likewise within the scope of the present invention.

The specific geometry of the present embodiment of the heat transfer pad 12 for the hip is evident with reference to FIGS. 2-8. As shown in FIG. 9, the system 10 optionally further comprises an upper retention strap 22, a lower retention strap 24 and associated releasable strap fasteners (not shown), which are preferably hook and loop fasteners. An exemplary releasable hook and loop fastener having utility herein is commercially available under the trademark VELCRO® which is a registered trademark of Velcro Industries B.V. for hook and loop fasteners. The straps 22, 24 and fasteners facilitate securing the pad 12 to the body of a patient once the pad 12 is applied to a treatment region as described below.

With additional reference to FIGS. 10A and 10B, mounting the heat transfer pad 12 on the hip 26 is effected by releasably fastening one end of each the upper and lower retention straps 22, 24 to the pad 12 while maintaining the opposite end of each strap 22, 24 free. An insulating barrier 28, such as a dressing, an elastic bandage, cast padding or the like, which may be configured in correspondence with the configuration of the pad 12, is preferably positioned atop the hip 26 before application of the pad 12 to the hip 26 as shown in FIG. 10A. The insulating barrier 28 desirably prevents direct contact between the skin of the patient and the heat transfer pad 12. Mounting the pad 12 is completed by applying the pad 12 to the hip 26 with the insulating barrier 28 preferably positioned therebetween and conforming the pad 12 to the contours of the hip 26 and adjacent neighboring body surfaces. The pad 12 is secured to the hip 26 by wrapping the upper retention strap 22 around the waist and the lower retention strap 24 around the thigh and releasably fastening the free ends of each the upper and lower retention straps 22, 24 to the pad 12 as shown in FIG. 10B. As such, the mounted pad 12 preferably does not block or unduly impair mobility of the patient about the waist or the hip. Once the pad 12 is mounted and secured, the pad 12 is coupled to the fresh fluid feed line 18 and spent fluid return line as shown in FIG. 10B for operation of the system 10 as described in detail below.

With continuing reference to FIG. 1, the heat transfer pad 12 includes pad inlet and outlet ports 30, 32 (shown in a partial cutaway) and a bladder 34 which is connectively positioned in fluid communication with the ports 30, 32. The bladder 34 encloses a tortuous internal flowpath for the heat transfer fluid which extends from the pad inlet port 30 to the pad outlet port 32 over essentially the entire surface area of the bladder 34. In operation, the reservoir 14 is positioned a distance apart from the heat transfer pad 12 with the fresh fluid feed and spent fluid return lines 18, 20 extending between the pad 12 and the reservoir 14. Accordingly, the fresh fluid feed and spent fluid return lines 18, 20 are each relatively long, e.g., on the order of about 1-2 m, to allow the user substantial freedom in selecting the relative positioning of the pad 12 and reservoir 14.

The fresh fluid feed line 18 draws heat transfer fluid at a non-ambient temperature from the reservoir 14, which is termed fresh heat transfer fluid, and charges the fresh heat transfer fluid to the pad 12. Conversely, the spent fluid return line 20 receives heat transfer fluid at a lower or higher temperature than the fresh heat transfer fluid from the pad 12, which is termed spent heat transfer fluid, and returns the spent heat transfer fluid to the reservoir 14. In the case of high temperature therapy, the spent heat transfer fluid has a lower temperature than the fresh heat transfer fluid because the fresh heat transfer fluid is cooled as it transfers heat to the patient. In the case of cold therapy, the spent heat transfer fluid has a higher temperature than the fresh heat transfer fluid because the fresh heat transfer fluid is heated as the patient transfers heat to it.

The fresh fluid feed and spent fluid return lines 18, 20 are each preferably constructed from a continuous length of the same flexible tubing material and each line 18, 20 preferably has essentially the same length. The lines 18, 20 can likewise have essentially the same cross-section or alternatively, the spent fluid return line 20 can have a smaller cross-section than the fresh fluid feed line 18 to create a fluid back pressure upstream of the spent fluid return line 20. A line sheath 36 extends essentially the length of the lines 18, 20 and encloses the two lines 18, 20, to form a single integrated tubing enclosure. The sheath 36 is constructed from a supple material which renders the entire tubing enclosure flexible. The sheath 36 has a durable exterior skin and an insulating foam interior which minimizes heat transfer between the fresh fluid feed line 18 and the spent fluid return line 20 or between the lines 18, 20 and their surrounding external environment. The sheath 36 also prevents condensate formation on the exterior of the lines 18, 20.

The reservoir 14 is a fluid container which has a carrying handle 37 and an open top 38 for the user to access the interior of the container. The open top 38 enables a user to manually add heat transfer fluid in bulk to the reservoir 14 when charging the system 10 or to manually withdraw heat transfer fluid in bulk from the reservoir 14 when draining the system 10. The reservoir 14 has insulated walls and a fitted removable insulated lid 40 for selectively covering the open top 38 and is thermally passive. The term "thermally passive", as used herein, characterizes a device which is free of any active structural cooling or heating elements, such as active refrigeration coils, heating coils, or the like, which actively cool or heat the heat transfer fluid. The entirety of the system 10 is likewise preferably characterized as thermally-passive insofar as the entire system 10 is preferably free of any active cooling or heating elements. Notwithstanding the above, it is within the scope of the present invention to place a passive heating or cooling medium in the reservoir 14. For example, crushed ice can be placed in the reservoir 14 as a passive cooling medium to passively cool the heat transfer fluid therein.

The pump 16 is generally any conventional means for performing the following functions in series: driving fresh heat transfer fluid from the reservoir 14 to the bladder 34 via the fresh fluid feed line 18 and pad inlet port 30; driving heat transfer fluid through the bladder 34; and returning spent heat transfer fluid from the bladder 34 to the reservoir 14 via the pad outlet port 32 and spent fluid return line 20. As such, the pump 16 can be selected from any number of well-known pumps having differing structures and mechanisms of operation. For example, the pump 16 can inter alia be an axial pump, a centrifugal pump, a gear pump, or a reciprocating pump. An exemplary pump having utility in the system 10 is a single-speed gear pump. A single-speed pump is defined herein as a pump having a pump motor which is permanently fixed at a single set operating speed when pumping against a minimal downstream resistance to flow. The single-speed pump lacks means for the user to adjust or reset the fixed operating speed of the pump motor once it has been fixed during manufacture.

In accordance with the embodiment of FIG. 1, the lid 40 integrally houses the pump 16. The pump 16 is preferably dc-powered by a transformer 42 which converts ac power from a conventional ac wall outlet to dc power. A power line 44 conveys the dc power from the transformer 42 to the dc pump motor (not shown) within the pump 16. A connector 46 is intermediately positioned in the power line 44 so that the transformer 42 can be separated from the lid 40 when the system 10 is not in operation. The connector 46 comprises a female jack mounted in the lid 40 and a cooperative male plug on the power line 44 which is releasably received in the jack. In one alternative to the present embodiment, the dc-powered pump can obtain power directly from a dc power source, such as a conventional battery, which obviates the transformer. In another alternative, the pump can be ac-powered enabling connection of the pump to an ac wall outlet via a power line which likewise obviates the transformer. In yet another alternative, the pump can be a variable-speed pump which is defined herein as a pump including means for the user to actively vary the operating speed of the pump motor. A pump speed control dial or similar manually-operated user input/output device can be provided which enables the user to actively control the pump speed.

In accordance with the present embodiment, the distal ends of the fresh fluid feed and spent fluid return lines 18, 20 engage the lid 40. The distal end of the fresh fluid feed line 18 extends into the lid 40 and is in fluid communication with an internal pumping chamber (not shown) of the pump 16. The internal pumping chamber is correspondingly in fluid communication with the reservoir 14 via a plurality of inlet ports 48 formed in the lid 40. The distal end of the spent fluid return line 20 likewise extends into the lid 40 and is in fluid communication with the reservoir 14 via an outlet port 50 formed in the lid 40. When the lid 40 is fitted over the open top 38 of the reservoir 14, the pump 16 is operatively positioned in the reservoir 14 with the inlet ports 48 submerged in the fresh heat transfer fluid residing therein.

Figure 11B:
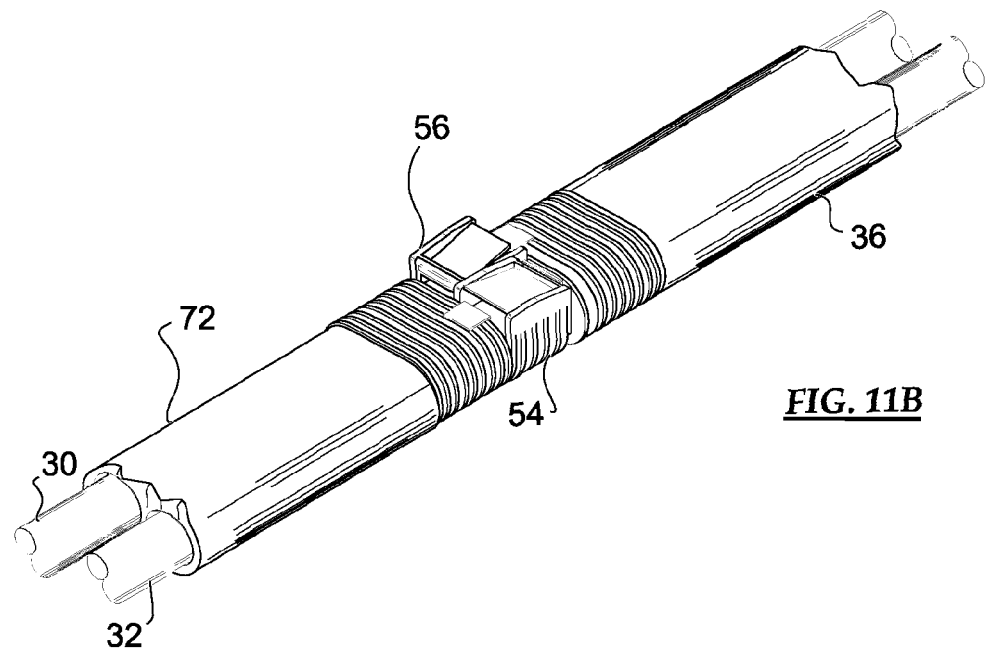
FIG. 11B is a perspective view of the coupled connective joint between the heat transfer pad and fluid lines of FIG. 1.
Figure 11A:
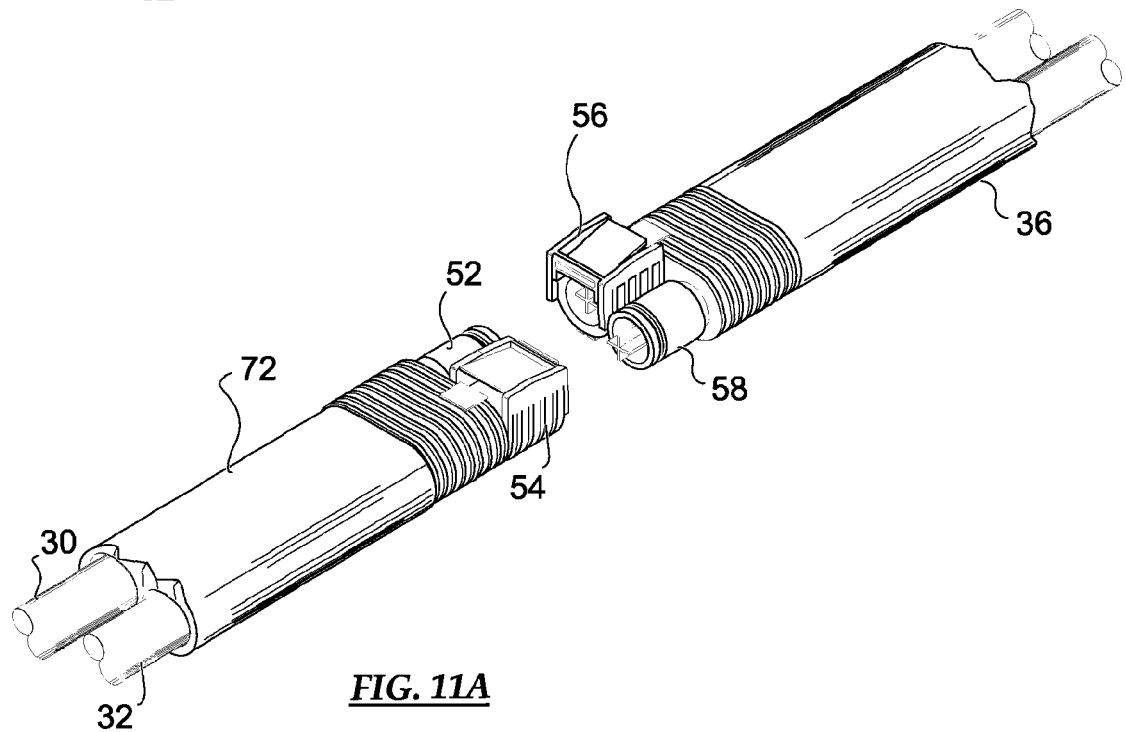
FIG. 11A is a perspective view of the uncoupled connective joint between the heat transfer pad and fluid lines of FIG. 1.

With additional reference to FIGS. 11A and 11B, the open distal ends of the pad inlet and outlet ports 30, 32 have inlet and outlet port couplings 52, 54, respectively, positioned across them. The inlet and outlet port couplings 52, 54 are configured to cooperatively and releasably mate with feed and return line couplings 56, 58, respectively, positioned across the open proximal ends of the fresh fluid feed and spent fluid return lines 18, 20. The terms "proximal end" and "distal end" are used in the present context relative to the bladder 34. The "proximal end" is more proximal to the bladder 34 and the "distal end" is more distal to the bladder 34. The couplings 52, 54, 56, 58 are preferably snap-action locking couplings which are selectively manually releasable by the user. The couplings 52, 54, 56, 58 preferably have inside diameters essentially corresponding to the inside diameter of the fresh fluid feed and spent fluid return lines 18, 20. The inlet and outlet port couplings 52, 54 are preferably a male coupling and a female coupling, respectively, and the feed and return line couplings 56, 58 are preferably a female and a male coupling, respectively. Although not shown, the inlet and outlet port couplings are alternatively a female coupling and a male coupling, respectively, while the feed and return line couplings are alternatively a male and a female coupling, respectively. In accordance with either configuration, the inlet port coupling 52 is preferably only mateable with the feed line coupling 56 to the exclusion of the return line coupling 58 and the outlet port coupling 54 is only mateable with the return line coupling 58 to the exclusion of the feed line coupling 56.

Mating the inlet port coupling 52 with the feed line coupling 56 and mating the outlet port coupling 54 with the return line coupling 58 forms a coupled connective joint between the heat transfer pad 12 and the fresh fluid feed and spent fluid return lines 18, 20 as shown in FIGS. 10B and 11B. The connective joint enables fluid communication between the pad inlet and outlet ports 30, 32 and the fresh fluid feed and spent fluid return lines 18, 20, respectively, as well as between the fresh fluid feed and spent fluid return lines 18, 20 and the internal flowpath of the bladder 34 which is integral with the pad inlet and outlet ports 30, 32.

Each inlet and outlet port coupling 52, 54, includes an integral shutoff valve which restricts fluid communication between the internal flowpath of the bladder 34 and the surrounding external environment via the pad inlet and outlet ports 30, 32 when the couplings 52, 54 are unmated from the couplings 56, 58. Accordingly, the integral shut off valves prevent fluid leakage from the pad 12 when the pad 12 is uncoupled from the fresh fluid feed and spent fluid return lines 18, 20. Each feed line and return line coupling 56, 58, similarly includes an integral shutoff valve which restricts fluid communication between the fresh fluid feed and spent fluid return lines 18, 20 and the surrounding external environment via the proximal ends of the lines 18, 20 when the couplings 56, 58 are unmated. The integral shut off valves similarly prevent fluid leakage from the lines 18, 20 when the lines 18, 20 are uncoupled from the pad 12. Each shutoff valve is normally biased in the closed position when the couplings 52, 54, 56, 58 are unmated. However, mating the inlet port coupling 52 with the feed line coupling 56 and the outlet port coupling 54 with the return line coupling 58 actively transitions each shutoff valve to the open position. When the shutoff valves are in the open position, they do not substantially impede flow through the couplings 52, 54, 56, 58. The above-described construction and operation of the couplings 52, 54, 56, 58 are similar to those disclosed in commonly-owned U.S. Pat. No. 5,232,020 to Mason et al., which is incorporated herein by reference.

Further details of the heat transfer pad 12 are shown and described below with additional reference to FIGS. 8 and 12-14. As noted above, the pad 12 comprises the bladder 34 and the pad inlet and outlet ports 30, 32. The bladder 34 has a substantially planar construction insofar as the bladder 34 has a thickness dimension which is very small relative to the length and width dimensions of the bladder 34. For example, the length and width dimensions of the bladder 34 are typically at least an order of magnitude greater than the thickness dimension of the bladder 34. More particularly, the bladder 34 of the present embodiment has an exemplary length of about 32 cm and an exemplary width of about 52 cm. In contrast the bladder 34 has an exemplary thickness on the order of only about 2-3 mm when empty, although the thickness of the bladder 34 expands somewhat when filled with heat transfer fluid during operation of the system 10 as described below.

The bladder 34 comprises an inner sheet 60 and an outer sheet 62. The terms "inner sheet" and "outer sheet" are used in the present context relative to the body of the patient. The "inner sheet" is more proximal to the patient and the "outer sheet" is more distal to the patient when the pad 12 is mounted on the patient. The inner and outer sheets 60, 62 are each formed from a pliant plastic film and are preferably identically shaped and sized to be superimposed one atop the other. The inner and outer sheets 60, 62 are bonded to one another along their common periphery by conventional means, such as welding or the like, to form an essentially continuous outer peripheral bond 64 which encloses and seals off the bladder 34 from the surrounding external environment. The inner and outer sheets 60, 62 are also bonded together along a plurality of straight and curved line segments which are interior to the outer peripheral bond 64 as described in greater detail below. The sum of these segment bonds and the outer peripheral bond 64 form a bond network.

The segment bonds have sufficient integrity to prevent the heat transfer fluid from flowing through them, thereby requiring the heat transfer fluid to flow around them within the bladder 34. Accordingly, the bond network encloses and defines the internal flowpath for the heat transfer fluid within the bladder 34. The internal flowpath is itself a continuous network of interconnected void spaces occupying the thickness between the inner and outer sheets 60, 62 where the sheets 60, 62 are unbonded to one another. It is readily apparent that the void space network has a configuration corresponding essentially identically to the configuration of the bond network. Particular characteristics of the internal flowpath, which are described in detail below, are features of the present invention.

The pad inlet and outlet ports 30, 32 are positioned adjacent to one another at the periphery of the bladder 34. The pad inlet port 30 provides a single inlet for the fresh heat transfer fluid into the internal flowpath of the bladder 34, while the pad outlet port 32 provides a single outlet for the spent heat transfer fluid from the internal flowpath of the bladder 34. The pad inlet port 30 includes an inlet tubing segment 66 having a proximal end which extends between the peripheries of the inner and outer sheets 60, 62 into the internal flowpath of the bladder 34. The pad outlet port 32 similarly includes an outlet tubing segment 68 having a proximal end which extends between the peripheries of the inner and outer sheets 60, 62 adjacent to the inlet tubing segment 66 into the internal flowpath of the bladder 34. The first and second tubing segments 66, 68 are preferably relatively short, e.g., on the order of about 15-20 cm, and are preferably constructed from the same flexible tubing material and having essentially the same cross-section as the fresh fluid feed and spent fluid return lines 18, 20.

The inner and outer sheets 60, 62 are permanently bonded to the proximal ends of the inlet and outlet tubing segments 66, 68 where the sheets 60, 62 and tubing segments 66, 68 intersect, thereby maintaining the continuity and integrity of the fluid seal along the outer peripheral bond 64 at the pad inlet and outlet ports 30, 32. The proximal ends of the inlet and outlet tubing segments 66, 68 extend into and are each open to the internal flowpath of the bladder 34. Although the present invention is not limited to any one specific configuration of the pad inlet and outlet ports 30, 32, the proximal ends of the tubing segments 66, 68 and the structures immediately surrounding them can be configured in whole or in part in a manner similar to that disclosed in U.S. Patent Application Publication No. 2008/0288033 A1 dated Nov. 20, 2008 incorporated herein by reference. Such a configuration provides a substantial resistance to occlusion of the ports 30, 32 when the ports 30, 32 are bent while the pad 12 is mounted on the patient. In any case, the distal ends of the inlet and outlet tubing segments 66, 68 extend away from the bladder 34 and have the inlet and outlet port couplings 52, 54, respectively, positioned across them. The inlet and outlet port couplings 52, 54 are configured to cooperatively and releasably mate with the feed and return line couplings 56, 58, respectively, as described above.

Although not shown, it is alternately within the scope of the present invention to construct each of the inlet and outlet tubing segments in two sections to facilitate of construction of the pad rather than to construct each of the tubing segments in one piece as shown in the drawings. In accordance with this alternate embodiment, the proximal ends of the inlet and outlet tubing segments can each be separate relatively short first tubing sections which are positioned during pad construction at the point where the pad inlet and outlet ports engage the bladder and extend into the bladder. After the outer peripheral bond is formed around the proximal end sections, the remaining sections of each inlet and outlet tubing segment are press fitted into the ends of the first sections and extend away from the bladder.

The heat transfer pad 12 is further provided with insulating means to diminish heat transfer between the pad 12 and its surrounding external environment and to correspondingly focus heat transfer between the pad 12 and the patient on which the pad 12 is mounted. In particular, an insulating sheet 70 is bonded to the outside face of the outer sheet 62 of the bladder 34 to perform the above-recited function. The insulating sheet 70 is preferably a cloth/foam laminate with the cloth layer of the laminate facing outwardly and the foam layer facing inwardly against the outer sheet 62. A port sheath 72 extends between the inlet and outlet port couplings 52, 54 and the bladder 34 and encloses the inlet and outlet tubing segments 66, 68. The port sheath 72 has substantially the same characteristics as the line sheath 36 and performs a substantially similar function, but with respect to the inlet and outlet tubing segments 66, 68 rather than the lines 18, 20.

The internal flowpath of the bladder 34 is characterized by an elongate inlet chamber 74 positioned at the interface of the pad inlet port 30 and a pair of flowpath partitions described in detail below. The inlet chamber has a first end 76 at the pad inlet port 30 on the lower part of the pad 12. The proximal end of the inlet tubing segment 66 opens directly into the first end 76 of the inlet chamber 74, thereby providing free unrestricted direct fluid communication between the pad inlet port 30 and the bladder 34, and more particularly the inlet chamber 74. As a result, the pad inlet port 30 discharges fresh heat transfer fluid directly into the inlet chamber 74 from the reservoir 14 via the fresh fluid feed line 18. In contrast, the inlet chamber 74 is physically isolated from the pad outlet port 32 by a segment bond termed a port divider bond 78.

An outlet chamber 80 of the internal flowpath is conversely positioned at the interface of the pad outlet port 32 and the pair of flowpath partitions noted above which are described in detail below. The proximal end of the outlet tubing segment 68 is directly open into outlet chamber 80, thereby enabling unrestricted direct fluid communication between the pad outlet port 32 and the bladder 34, and more particularly the outlet chamber 80. However, the proximal end of the outlet tubing segment 68 lacks unrestricted direct fluid communication with the inlet chamber 74. As a result, the pad outlet port 32 receives spent heat transfer fluid from the outlet chamber 80 as described below. The port divider bond 78 substantially prevents unrestricted direct fluid communication between the pad outlet port 32 and the inlet chamber 74 by extending longitudinally between the proximal ends of the inlet and outlet tubing segments 66, 68 in essentially the same orientation as the tubing segments 66, 68. The bond 78 physically isolates the proximal ends of the tubing segments 66, 68 from one another, thereby essentially preventing the commingling of fresh and spent heat transfer fluid at the pad inlet and outlet ports 30, 32.

The inlet chamber 74 extends almost the entire length of the pad 12 along the central longitudinal axis of the pad 12, which is substantially vertically oriented when the pad 12 is mounted on the patient. The inlet chamber 74 has a relatively long narrow configuration with its length and width typically differing from one another by an approximate order of magnitude. For example, the inlet chamber 74 of the present embodiment has a length of about 26 cm and a width of about 3 cm. By comparison, the entire bladder 34 has a length similar in magnitude to the inlet chamber 74, e.g., about 32 cm, but has a much greater width, e.g., about 52 cm. The longitudinal sides of the inlet chamber 74 are bounded by a pair of parallely opposing segment bonds termed first and second inlet chamber bonds 82, 84. The bonds 82, 84 extend toward a second end 86 of the inlet chamber 74 which is on the upper part of the pad 12 opposite the first end 76 of the inlet chamber 74. The second end 86 is alternately termed a distal end because of its greater linear distance from the pad ports 30, 32 relative to the first end 76, which is alternately termed a proximal end because of its lesser linear distance from the pad ports 30, 32.

Another segment bond, termed an inner peripheral bond 88, extends around a substantial portion of the periphery of the pad 12 essentially parallel to the outer peripheral bond 64 spaced an essentially constant distance inward from the outer peripheral bond 64. In particular, the inner peripheral bond 88 extends essentially continuously around the opposing sides of the pad 12 and the top of the pad 12 positioned between the opposing sides. The terms "inner bond" and "outer bond" are used in the present context to designate their relative positioning in the interior of the pad plane. Thus, "inner" is closer to the pad interior and "outer" is closer to the pad periphery.

The inlet chamber 74 is bounded at its second end 86 by the inner peripheral bond 88. However, the first and second inlet chamber bonds 82, 84 do not extend all the way up to the inner peripheral bond 88, instead stopping a relatively small distance short of the inner peripheral bond 88, e.g., a distance on the order of about 1-2 cm. This gap between the upper (distal) ends of the first and second inlet chamber bonds 82, 84 and the inner peripheral bond 88 at the second end 86 of the inlet chamber 74 provides opposing first and second flow openings 90, 92 in the sides of the inlet chamber 74. The first and second flow openings 90, 92 are essentially mirror images of one another, being essentially identically sized and opposingly positioned relative to one another.

The first flow opening 90 opens with essentially no restriction into a first flowpath partition 94 of the internal flowpath of the bladder 34 and the second flow opening 92 opens with essentially no restriction into a second flowpath partition 96 of the internal flowpath of the bladder 34. The first and second flowpath partitions 94, 96 are separated by the inlet chamber 74 extending along the central longitudinal axis of the pad 12, so that each partition 94, 96 resides in an opposing half of the heat transfer pad 12, respectively (with the exception of a trailing portion of the second partition 96 described below). Furthermore, each partition 94, 96 occupies essentially the entirety of its half of the pad 12 (likewise with the exception of the trailing portion of the second partition 96).

Each flowpath partition 94, 96 excepting of the trailing portion of the second partition 96 has a configuration which is essentially a mirror image of the other. The first flowpath partition 94 is a single continuous undivided flow channel with distinct flow boundaries defined by the bond network. The bond network gives the flow channel a clearly defined continuous containment width along the entire length of the flow channel. As such, the containment width of the flow channel is essentially constant, i.e., has very limited variability, e.g., the containment width is within a range on the order of about 1-2 cm. The first partition 94 tortuously covers substantially the entire area of its half of the pad 12 before reaching a first partition terminus 98. Specifically, the first partition 94 doubles back and forth against itself between the first flow opening 90 and the first partition terminus 98 to form a series of side-by-side switchback sections 100 which enable counter-current flow from one switchback section to the next adjoining switchback section in series (as indicated by the directional flow arrows depicted in FIG. 12). The opposite upper and lower ends of each switchback section 100 extend proximal to the upper and lower periphery of the pad 12 so that there are minimal coverage gaps on the half of the pad 12 occupied by the first partition 94.

The switchback sections 100 are bounded in part by the substantially horizontally oriented (when the pad 12 is mounted on the patient) lengths of the outer and inner peripheral bonds 64, 88 and in part by additional substantially vertically oriented segment bonds, termed common switchback bonds 102, which are orthogonally oriented relative to peripheral bonds 64, 88. Like the upper (distal) ends of the first and second inlet chamber bonds 82, 84, both the upper (distal) and lower (proximal) ends of the common switchback bonds 102 extend vertically across the pad 12 toward, but not all the way up to the inner peripheral bond 88, providing a gap at the upper (distal) and lower (proximal) ends of each switchback section 100. Accordingly, every time the heat transfer fluid in the first partition 94 reaches the end of a switchback section 100, it flows through the gap into the next adjoining switchback section 100 where the fluid reverses its flow direction and continues through that switchback section 100 toward the first partition terminus 98. This flow pattern is serially repeated in each switchback section 100 until the heat transfer fluid in the first partition 94 has serially navigated each and every switchback section 100 in the first partition 94 and has reached the first partition terminus 98. It is noted that the common switchback bonds 102 block commingling of heat transfer fluid in adjoining switchback sections 100 with one another, thereby essentially preventing fluid back mixing in the first partition 94.

Although the present invention is not limited to any particular model for flow within the internal flowpath of the bladder 34, it is believed that the flow of heat transfer fluid within the first partition 94 approximates a plug flow model at least in gross. In particular, it is believed that each discrete instantaneous volume of heat transfer fluid entering the first partition 94 via the first flow opening 90 at a given point in time tends to reach the first partition terminus 98 at essentially one single later point in time.

The second flowpath partition 96 is likewise a single continuous undivided flow channel having substantially the same characteristics as the first partition 94, but on the opposite half of the pad 12 from the first partition 94. As such, the second partition 96 tortuously doubles back and forth against itself between the second flow opening 92 and a second partition terminus 104 in a series of side-by-side switchback sections 100 which make up a lead portion 106 of the second partition 96 that is essentially identical to the first partition 94. However, the second partition 96 differs from the first partition 94 in that the second partition 96 also has a trailing portion 108 which is absent from the first partition 94. The trailing portion 108 serially follows the tortuous lead portion 106. Whereas substantially the entirety of the first partition 94 is characterized as relatively tortuous, the trailing portion 108 of the second partition 96 is characterized as relatively long and non-tortuous. The non-tortuous trailing portion 108 is bounded on one side by the outer peripheral bond 64 and on the other side by the inner peripheral bond 88. The trailing portion 108 extends the single continuous undivided flow channel of the second partition 96 which is initiated by the lead portion 106 all the way to the second partition terminus 104 and maintains the same essentially constant width throughout its length. The trailing portion 108 is alternately termed the fluid return loop and enables the desired positioning of the first and second partition terminuses 98, 104 adjacent to one another at essentially the same point in the bladder 34.

The first and second partition terminuses 98, 104 are both openings into the outlet chamber 80 at a first (distal) end 110 of the outlet chamber 80 which is opposite a second (proximal) end 112 of the outlet chamber 80. However, unlike the unrestricted first and second flow openings 90, 92, the first and second partition terminuses 98, 104 have first and second flow restrictors 114, 116, respectively, mounted therein which restrict the flow of heat transfer fluid through the partition terminuses 98, 104. The first and second flow restrictors 114, 116 are mounted in the first and second partition terminuses 98, 104 of the bladder 34 in a manner similar to mounting the proximal ends of the inlet and outlet tubing segments 66, 68 in the bladder 34. In particular, the first and second flow restrictors 114, 116 are positioned in their respective first and second partition terminuses 98, 104 during construction of the pad 12 and the outer and inner peripheral bonds 64, 88 are integrally formed around both flow restrictors 114, 116 to snugly fit the flow restrictors 114, 116 between the inner and outer sheets 60, 62. As a result, the position of the first and second flow restrictors 114, 116 within the bladder 34 is secured at the first and second partition terminuses 98, 104.

Figure 13:
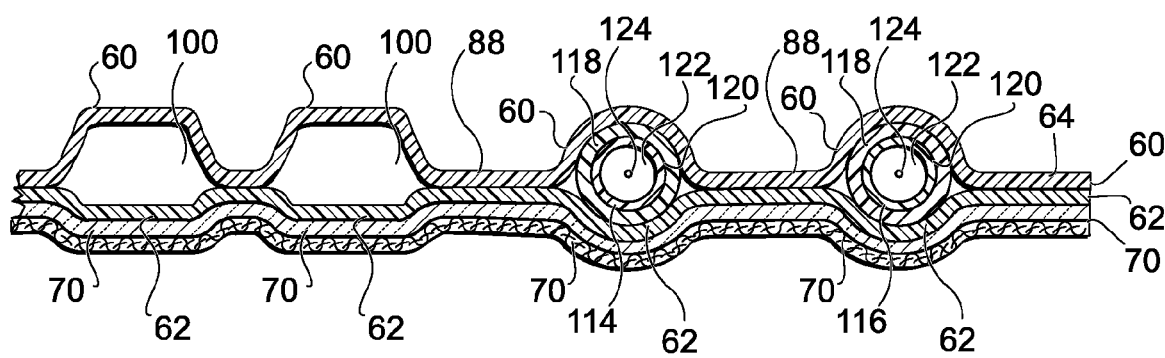
FIG. 13 is a conceptualized elevation view in section of the heat transfer pad taken at 13-13 in FIG. 1.
Figure 14:
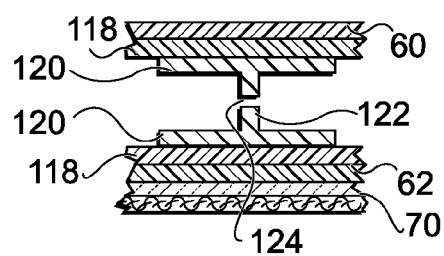
FIG. 14 is a conceptualized side elevation view in section of a flow restrictor in the heat transfer pad of the present invention.

The outer and inner peripheral bonds 64, 88 form a fluid-tight seal around the first and second flow restrictors 114, 116 so that all of the heat transfer fluid in the first and second flowpath partitions 94, 96 must flow through the first and second flow restrictors 114, 116, respectively, to enter the outlet chamber 80 of the bladder 34. The first and second flow restrictors 114, 116 are essentially identical to one another, both structurally and functionally. Accordingly, the first flow restrictor 114 is described in detail below with specific reference to FIGS. 13 and 14, it being understood that the same description applies equally to the second flow restrictor 116. It is noted that FIGS. 13 and 14 are conceptualized views in which the scale of certain features is modified from that of the remaining FIGS. for purposes of illustration.

The first flow restrictor 114 comprises an outer tubing segment 118 and an inner tubing segment 120 which is concentrically nested within the outer tubing segment 118. The inner and outer tubing segments 118, 120 are preferably relatively short and of equal length, e.g., on the order of about 1 cm. The primary function of the outer tubing segment 118 is to facilitate mounting of the inner tubing segment 120 within the opening of the first partition terminus 98 as described above. The outer tubing segment 118 is preferably formed from the same flexible tubing material as the first and second tubing segments 66, 68 and the fresh fluid feed and spent fluid return lines 18, 20 and preferably has essentially the same cross-section.

The inner tubing segment 120 has an outside diameter in substantial correspondence with the inside diameter of the outer tubing segment 118 so that the inner tubing segment 120 can be press fitted into the outer tubing segment 118 and securely retained therein while preventing substantial leakage of heat transfer fluid between the outer and inner tubing segments 118, 120. The inner tubing segment 120 is preferably molded from a relatively more rigid plastic than the outer tubing segment 118. Accordingly, the inner tubing segment 120 maintains its tubular configuration and substantially resists deformation during normal use of the pad 12 within the system 10, thereby avoiding occlusion of the first flow restrictor 114 even when the pad 12 is being conformed to the contours of a patient. The inner tubing segment 120 is characterized by the presence of a diaphragm 122 across its entire inside diameter. An exemplary inside diameter of the inner tubing segment 120 is on the order of about 3 or 4 mm. A single orifice 124 extends through the center of the diaphragm 122 which provides the sole passageway for the heat transfer fluid from the first partition 94 to the outlet chamber 80. The orifice 124 is preferably a tiny pinhole opening in the diaphragm 122 which has a diameter at least an order of magnitude smaller than the inside diameter of the inner tubing segment 120. As such, the above-specified construction of the first flow restrictor 114 creates a significant heat transfer fluid back pressure in the first partition 94 behind the first flow restrictor 114

Although, as stated above, the present invention is not limited to any one heat transfer pad configuration, the present exemplary embodiment of a heat transfer pad 12 has a specific configuration which is adaptable to the surface contours of a hip and its neighboring body surfaces with the objectives of providing optimal non-ambient temperature therapy to the hip without unduly restricting the mobility of the patient about the waist and corresponding hip joint. To achieve these objectives, the pad 12 has an essentially symmetrical geometric configuration about its central longitudinal axis. Each essentially identical half of the pad 12 is characterized by an indent 126 along the side edge of the pad. The indent 126 is significantly sized relative to the overall size of the pad 12 and has a concave C-shape. The indent 126 defines an upper (distal) wing 128 of the pad 12 which is positioned above the indent 126 and distal to the ports 30, 32 when the pad 12 is mounted on a patient. The indent 126 also defines a lower (proximal) wing 130 which is positioned below the indent 126 and proximal to the ports 30, 32 when the pad 12 is mounted on a patient. It is readily apparent from FIGS. 10A and 10B that the indents 126 facilitate mobility of the patient when the pad 12 is mounted on the patient while the wings 128, 130 enhance the effectiveness of the therapy by maximizing the surface area of the pad 12 contacting the desired treatment region of the body.

Normal steady-state operation of the system 10 entails drawing fresh heat transfer fluid from the reservoir 14 through the fresh fluid feed line 18 under the power of the pump 16 and charging the fresh heat transfer fluid to the pad 12 mounted on the patient via the pad inlet port 30. The pad inlet port 30 discharges the fresh heat transfer fluid directly into the first end 76 of the inlet chamber 74 where heat transfer promptly begins to occur between the patient and the fresh heat transfer fluid. The heat transfer fluid begins to transition from a fresh heat transfer fluid to a spent heat transfer fluid at the moment heat transfer begins to occur across the surface of the inner sheet 60 which is in indirect contact with the desired treatment region of the body across the intervening insulating barrier 28 for the comfort and safety of the patient.

Once in the first end 76 of the inlet chamber 74, the fresh heat transfer fluid is displaced by the pump 16 up through the inlet chamber 74 to the second end 86 thereof and further displaces the fresh heat transfer fluid out through the first and second flow openings 90, 92 at the second end 86. It has been found that displacement of the heat transfer fluid through the first and second flow openings 90, 92 effectively bifurcates the heat transfer fluid feed to the pad 12 into two essentially equal flow streams of heat transfer fluid. The first flow stream is diverted by the inner peripheral bond 88 through the first flow opening 90 into the first flowpath partition 94 at a first flow rate while the second flow stream is simultaneously diverted by the inner peripheral bond 88 through the second flow opening 92 into the second flowpath partition 96 at a second flow rate which is preferably essentially equal to the first flow rate.

The first flow stream, although continuous, may be characterized as a series of first instantaneous volumes of heat transfer fluid, which serially navigate the switchback sections 100 of the first partition 94. The second flow stream, although also continuous, may similarly be characterized as a series of second instantaneous volumes of heat transfer fluid which, simultaneous with the first instantaneous volumes of heat transfer fluid, serially navigate the switchback sections 100 of the second partition 96 at essentially the same flow rate as the first instantaneous volume. All the while heat transfer continues between the patient and the first and second volumes of heat transfer fluid until the heat transfer fluid essentially equilibrates to the body temperature of the patient or the heat transfer fluid is discharged from the bladder 34, thereby completing the transition of fresh heat transfer fluid to spent heat transfer fluid within the pad 12.

The spent heat transfer fluid is discharged from the bladder 34 via the outlet chamber 80 and pad outlet port 32. The pump 16 thereafter displaces the spent heat transfer fluid from the pad outlet port 32 through the spent fluid return line 20, which returns the spent heat transfer fluid to the reservoir 14. The returned spent heat transfer fluid mixes with the fresh heat transfer fluid in the reservoir 14 which effectively functions as a heat sink. The fresh heat transfer fluid in the reservoir 14 essentially reverses any temperature increase or decrease in the returned spent heat transfer fluid caused by heat transfer with the body by reason of the significantly smaller volume of spent heat transfer fluid relative to fresh heat transfer fluid in the reservoir 14. Accordingly, the reservoir 14 essentially regenerates fresh heat transfer fluid from returned spent heat transfer fluid.

Figure 12:
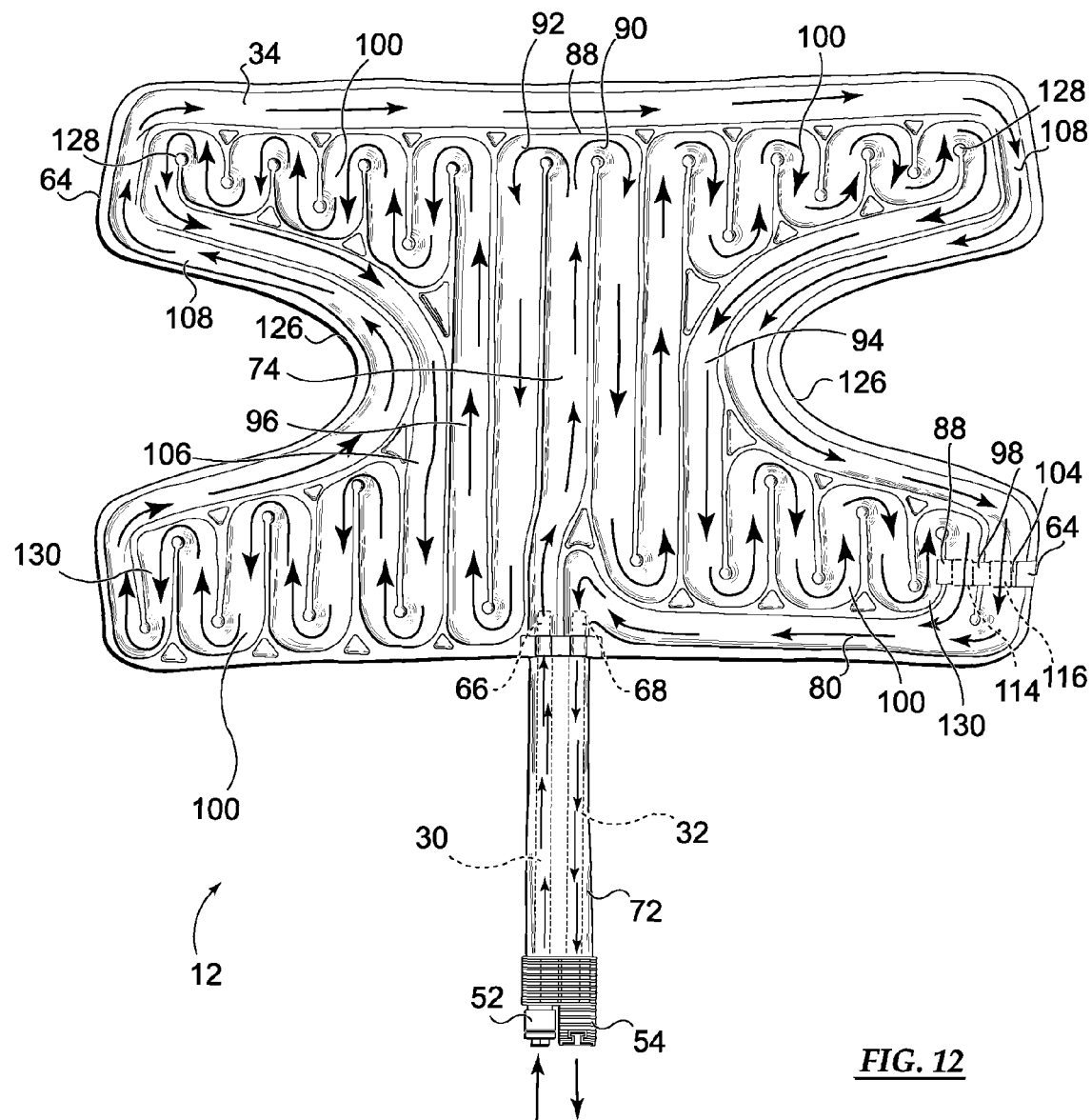
FIG. 12 is a front view of the heat transfer pad of FIG. 1 with directional arrows to depict the flow of heat transfer fluid through the pad.

It is apparent from the directional flow arrows depicted in FIG. 12, that a heat transfer gradient will exist in the pad 12 which is indirectly correlated to the distance that any given point in the internal flowpath of the bladder 34 is away from the pad inlet port 30. In other words, the greater the distance the heat transfer fluid has traveled through the internal flowpath of the bladder 34 away from the pad inlet port 30, the lower the rate of heat transfer between the heat transfer fluid and the body of the patient at that point. This phenomenon is attributable to the fact that the temperature of the heat transfer fluid continuously approaches closer to equilibrium with the temperature of the body as the heat transfer fluid travels through the internal flowpath of the bladder 34 further away from the pad inlet port 30, which progressively diminishes the rate of heat transfer between the heat transfer fluid and the body.

The present invention recognizes that a heat transfer pad, which is adapted for mounting on a particular desired treatment region of the body, will not only contact the desired treatment regions when mounted on the body, but will also inherently contact neighboring adjacent regions of the body where therapy is less desired and/or needed. Accordingly, the present invention enables the practitioner to configure the internal flowpath in the bladder of the heat transfer pad so that localized surface areas on the pad having a relatively high heat transfer rate are specified. These specified localized surface areas correspond identically to the same localized surface areas on the pad which contact the desired treatment region of the body when the pad is mounted thereon. Conversely, the localized surface areas on the pad having a relatively low heat transfer rate correspond to the localized surface areas on the pad which contact regions on the body where therapy is less desired and/or necessary. Thus, the present invention enables the practitioner to optimize the overall therapeutic effectiveness of the non-ambient temperature therapy system.

Using the present embodiment of the heat transfer pad 12 as a specific example for the teaching of the invention, it is predetermined that the optimal desired treatment region for an afflicted hip 26 is a side surface of the body overlying the afflicted hip. Accordingly, the heat transfer pad 12 is constructed as shown and described herein so that the pad 12 inter alia contacts this specific desired treatment region as well as other neighboring adjacent regions of the body when the pad 12 is mounted thereon. The practitioner then determines that the particular localized surface area of the pad 12 which comes into contact with the side surface of the body corresponding to the afflicted hip 26 is the localized surface area proximal to the central longitudinal axis of the pad 12. Therefore, the practitioner designs the configuration of the bladder 34 in the pad 12 so that a relatively high local heat transfer rate is achieved in the portion of the internal flowpath proximal to the central longitudinal axis of the pad 12, i.e., in the inlet chamber 74 and the immediately adjoining switchback sections 100 of the first and second flowpath partitions 94, 96. When the resulting pad 12 is mounted on the body, this portion of the internal flowpath is in close contact with the surface of the hip 26 where therapy is most desired, thereby optimizing the therapeutic effectiveness.

It is further predetermined that additional desired treatment regions for the afflicted hip 26 are the front and back surfaces of the body which are immediately adjacent to the hip 26. Accordingly, the practitioner determines that the particular localized surface areas of the pad 12 which come into contact with these surfaces of the body correspond to the upper (distal) wings 128 of the first and second flowpath partitions 94, 96. Consequently, the practitioner designs the configuration of the bladder 34 so that an adequate local heat transfer rate is achieved in the upper (distal) wings 128. Although the local heat transfer rate diminishes as the switchback sections 100 of the first and second flowpath partitions 94, 96 extend into the upper (distal) wings 128, there is still a significant local heat transfer rate between the upper (distal) wings 128 and the front and back surfaces of the body above the hip 26. As a result, when the pad 12 is mounted on the body, the upper (distal) wings 128 are in close contact with the surface of the body above the hip 26 where therapy is also desired, thereby enhancing the therapeutic effectiveness.

It is still further predetermined that although the pad 12 comes into contact with the front and back surfaces of the body immediately below the hip 26, therapy is less desired or necessary for these surfaces. Accordingly, the practitioner designs the configuration of the bladder 34 so that relatively low local heat transfer rates occur in the lower (proximal) wings 130 of the first and second flowpath partitions 94, 96, which are the localized surface areas of the pad 12 coming into contact with the front and back surfaces immediately below the hip 26. Consequently, when the resulting pad 12 is mounted on the body, the lower (proximal) wings 130 do not detract from the therapeutic effectiveness of the other portions of the internal flowpath which come into contact with the surfaces of the body where therapy is desired. It is understood that in the present context the term "contact" embodies indirect contact between a heat transfer pad and the skin of a patient across an insulating barrier.

It is additionally noted that the first and second flow restrictors 114, 116 also enhance the effectiveness of the heat transfer pad 12 as a therapeutic device. From the standpoint of therapeutic effectiveness, it has been found desirable to maintain essentially equal flow rates of heat transfer fluid in the first and second flowpath partitions 94, 96. Otherwise, the consistency of local heat transfer rates are undesirably disrupted. Although the present configuration of the heat transfer pad 12 results in two essentially equal flow streams moving through the first and second flowpath partitions 94, 96, there are still some inherent differences between the configuration of the first and second flowpath partitions 94, 96, which from time to time can disrupt this equality. For example, the presence of the fluid return loop 108 at the end of the second partition 96 can at times create differences in the fluid back pressure exhibited within the two flowpath partitions 94, 96. Even a slight difference in back pressure between the two flowpath partitions 94, 96 can disrupt the flow rates of the heat transfer fluid within the two flowpath partitions 94, 96 and correspondingly disrupt the temperature gradients within the flowpath partitions 94, 96.

Unequal back pressures in the two flowpath partitions 94, 96 can be caused not only by inherent differences in the flowpath partition configurations as noted above, but also by occlusions in one of the flowpath partitions 94, 96. If one side of the pad 12 becomes crimped or otherwise occluded at any point in its flowpath partition 94 or 96, which can be a common occurrence during normal operation, the increased fluid back pressure upstream of the occlusion and the attendant pressure drop downstream of the occlusion on the the side of the pad 12 experiencing the occlusion could cause a substantial disparity in the flow rate of heat transfer fluid on the opposing sides of the pad 12. In particular, an occlusion on one side of the pad 12 will cause the diversion of most or all of the fresh heat transfer fluid in the inlet chamber 74 into the opposite unoccluded side of the pad 12 due to the disparity in back pressure between the two sides. It is understood that the term "occlusion" is used in the present context to include an impediment to fluid flow within a channel which substantially limits flow through the channel, but does not completely halt fluid flow therethrough.

The undesirable scenario of unequal flow rates of heat transfer fluid in the first and second flowpath partitions 94, 96 is avoided by the presence of the first and second flow restrictors 114, 116 on opposing sides of the pad 12, respectively, which apply an essentially equal fluid back pressure to the first and second flowpath partitions 94, 96 on opposing sides of the pad 12. This equal back pressure within the first and second flowpath partitions 94, 96 is attributable to the effect of the first and second flow restrictors 114, 116. In particular, each flow restrictor 114, 116 represents the greatest restriction point (i.e., the point having the greatest resistance to flow) in its respective flowpath partition 94, 96. Thus, the first flow restrictor 114 constitutes a greater restriction in the first flowpath partition 94 than any other inherent restrictions in the first flowpath partition 94 attributable to its configuration. The second flow restrictor 116 likewise constitutes a greater restriction in the second flowpath partition 96 than any other inherent restrictions in the second flowpath partition 96 attributable to its configuration. As a result, the substantial and equal fluid back pressure caused by the flow restrictors 114, 116 will override the effects of inherent differences in the geometry of the two sides of the pad 12.

Furthermore, if an occlusion occurs on one side of the pad 12 upstream of the flow restrictor, the increased back pressure upstream caused by the occlusion will also likely be less than the back pressure attributable to the flow restrictors 114, 116 on both sides of the pad 12. Since the back pressure caused by the flow restrictors 114, 116 will override the back pressure on any one side of the pad 12 caused by an occlusion, the fresh heat transfer fluid in the inlet chamber 74 will remain diverted to both sides of the pad 12 at essentially the same rate and the side of the pad 12 experiencing the occlusion will not exhibit a substantial reduction in the flow rate of heat transfer fluid therethrough.

While the forgoing preferred embodiments of the invention have been described and shown, it is understood that alternatives and modifications, such as those suggested and others, may be made thereto and fall within the scope of the invention.

We claim:

1. A heat transfer pad comprising:
 a bladder having an internal flowpath for a flow stream of a heat transfer fluid, said bladder having a first side edge, a second side edge, a central longitudinal axis between said first side edge and said second side edge and an inlet chamber extending along said central longitudinal axis to an inlet chamber termination at a first flow opening and a second flow opening, both said first flow opening and said second flow opening in fluid communication with said inlet chamber,
 wherein said inlet chamber has a first longitudinal sidewall and a second longitudinal sidewall enclosing opposing sides of said inlet chamber to enable flow of a heat transfer fluid therethrough in an inlet chamber direction,
 wherein each of said longitudinal sidewalls is continuous and fluid-impermeable to prevent said heat transfer fluid from exiting said inlet chamber except at said first flow opening and said second flow opening,
 wherein said inlet chamber bisects said bladder into a first half and a second half and divides said internal flowpath into a tortuous first flow channel at said first opening through which a first portion of said flow stream of said heat transfer fluid flows and a tortuous second flow channel at said second opening through which a second portion of said flow stream of said heat transfer fluid flows, wherein each of said flow channels is in fluid isolation from the other along essentially the entirety of its length, wherein said first flow channel occupies essentially the entirety of said first half of said bladder and said second flow channel occupies essentially the entirety of said second half of said bladder, wherein said first flow channel has a first series of successive side-by-side switchback sections, wherein said first series has a first side-by-side switchback section extending from said first flow opening and doubling back longitudinally alongside said inlet chamber in adjoining relationship thereto, thereby enabling flow of said heat transfer fluid through said first side-by-side switchback section of said first series in a first first series direction counter-current to said inlet chamber direction, wherein said second flow channel has a second series of successive side-by-side switchback sections, and wherein said second series has a first side-by-side switchback section extending from said second flow opening and doubling back longitudinally alongside said inlet chamber in adjoining relationship thereto on a side of said inlet chamber opposite said first side-by-side switchback section of said first series, thereby enabling flow of said heat transfer fluid through said first side-by-side switchback section of said second series in a first second series direction counter-current to said inlet chamber direction and co-current to said first first series direction;

an inlet port into said bladder for feeding fresh heat transfer fluid to said inlet chamber; and an outlet port out of said bladder for discharging spent heat transfer fluid from said bladder.

2. The heat transfer pad of claim 1, wherein essentially the entirety of said flow stream is divided into two essentially equal portions, wherein one of said two essentially equal portions is said first portion of said flow stream and the other of said two essentially equal portions is said second portion of said flow stream, wherein essentially all of said first portion is directed into said first flow channel via said first flow opening and essentially all of said second portion is directed into said second flow channel via said second flow opening adjacent to said first flow opening, and wherein essentially all of said first portion remains in said first flow channel until discharge therefrom via a first partition terminus upstream of said outlet port and essentially all of said second portion remains in said second flow channel flow until discharge therefrom via a second partition terminus upstream of said outlet port.

3. The heat transfer pad of claim 2, wherein said first flow channel is undivided so that said first portion of said flow stream remains a single continuous undivided stream within said first flow channel.

4. The heat transfer pad of claim 2, wherein said second flow channel is undivided so that said second portion of said flow stream remains a single continuous undivided stream within said second flow channel.

5. The heat transfer pad of claim 1, wherein said first and second flow channels are configured as essentially mirror images of one another on opposite halves of said bladder.

6. The heat transfer pad of claim 1 further comprising an outlet chamber connecting said outlet port and said first and second flow channels, wherein said first portion of said flow stream flows from said first flow channel into said outlet chamber via a first partition terminus and said second portion of said flow stream flows from said second flow channel into said outlet chamber via a second partition terminus.

7. The heat transfer pad of claim 6 further comprising a first flow restrictor positioned in said first partition terminus and a second flow restrictor positioned in said second partition terminus, wherein said first and second flow restrictors are configured to create back pressures in said first and second flow channels, respectively.

8. The heat transfer pad of claim 1, wherein said inlet port is positioned at said central longitudinal axis of said bladder.

9. The heat transfer pad of claim 1, wherein said outlet port is positioned at said central longitudinal axis of said bladder.

10. The heat transfer pad of claim 1, wherein said first series of successive side-by-side switchback sections has a second side-by-side switchback section extending from said first side-by-side switchback section of said first series and doubling back longitudinally alongside said first side-by-side switchback section of said first series in adjoining relationship thereto and closer to said first side edge of said bladder, thereby enabling flow of said heat transfer fluid through said second side-by-side switchback section of said first series in a second first series direction co-current to said inlet chamber direction and counter-current to said first first series direction and said first second series direction.

11. The heat transfer pad of claim 10, wherein said second series of successive side-by-side switchback sections has a second side-by-side switchback section extending from said first side-by-side switchback section of said second series and doubling back longitudinally alongside said first side-by-side switchback section of said second series in adjoining relationship thereto and closer to said second side edge of said bladder, thereby enabling flow of said heat transfer fluid through said second side-by-side switchback section of said second series in a second second series direction counter-current to said first second series direction and said first first series direction and co-current to said inlet chamber direction and said second first series direction.

12. The heat transfer pad of claim 1, wherein said bladder has a local heat transfer rate gradient centered at said central longitudinal axis and extending perpendicularly outward in opposing directions therefrom toward said first side edge of said bladder and toward said second side edge of said bladder and wherein local heat transfer rate of said bladder diminishes as said local heat transfer gradient extends away from said central longitudinal axis in opposing directions toward said first and second side edges.

13. The heat transfer pad of claim 1, wherein said bladder exhibits a highest local heat transfer rate at a central longitudinal region of said bladder containing said inlet chamber and said first switchback sections of said first and second series on opposing sides of said inlet chamber.

14. The heat transfer pad of claim 13, wherein said bladder exhibits a lower local heat transfer rate at a region of said bladder more proximal said first and second side edges of said bladder than said central longitudinal region.

15. The heat transfer pad of claim 1, wherein said inlet chamber extends along said central longitudinal axis at least almost the entire length of said bladder to said inlet chamber termination.

16. A heat transfer pad comprising:
a bladder having a planar configuration with an overall planar area, a central longitudinal axis, and a periphery, wherein said bladder has an opposing first side with a first planar area and an opposing second side with a second planar area, and wherein said opposing first side is positioned on the opposite side of said central longitudinal axis from said opposing second side;

a heat transfer fluid inlet chamber extending along said central longitudinal axis of said bladder from an inlet chamber start point proximal to a first end of said central longitudinal axis to an inlet chamber endpoint proximal to a second end of said central longitudinal axis, wherein said inlet chamber has a first longitudinal sidewall and a second longitudinal sidewall enclosing opposing sides of said inlet chamber to enable flow of a heat transfer fluid therethrough in an inlet chamber direction;

a heat transfer fluid inlet manifold centrally positioned within said bladder at said inlet chamber endpoint for receiving a volume of a heat transfer fluid therefrom, wherein said inlet manifold has a first flow opening and a second flow opening, and wherein each of said longitudinal sidewalls of said inlet chamber is continuous and fluid-impermeable to prevent said heat transfer fluid from exiting said inlet chamber except at said first flow opening and said second flow opening;

a heat transfer fluid outlet positioned downstream of said inlet manifold for receiving said volume of said heat transfer fluid from said first flow channel and said second flow channel and discharging said volume of said heat transfer fluid from said bladder;

a tortuous first flow channel extending between said first flow opening of said inlet manifold and said heat transfer fluid outlet, a majority of said first flow channel occupying said opposing first side of said bladder and said first flow channel receiving a first portion of said volume of said heat transfer fluid from said inlet manifold; and a tortuous second flow channel extending between said second flow opening of said inlet manifold and said heat transfer fluid outlet, a majority of said second flow channel occupying said opposing second side of said bladder and said second flow channel receiving a second portion of said volume of said heat transfer fluid from said inlet manifold, wherein said second flow channel is in fluid isolation from said first flow channel except at said heat transfer fluid outlet, wherein said first flow channel has a first series of successive side-by-side switchback sections, wherein said first series has a first side-by-side switchback section extending from said first flow opening and doubling back longitudinally alongside said inlet chamber in adjoining relationship thereto, thereby enabling flow of said heat transfer fluid through said first side-by-side switchback section of said first series in a first first series direction counter-current to said inlet chamber direction, wherein said second flow channel has a second series of successive side-by-side switchback sections, and wherein said second series has a first side-by-side switchback section extending from said second flow opening and doubling back longitudinally alongside said inlet chamber in adjoining relationship thereto on a side of said inlet chamber opposite said first side-by-side switchback section of said first series, thereby enabling flow of said heat transfer fluid through said first side-by-side switchback section of said second series in a first second series direction counter-current to said inlet chamber direction and co-current to said first first series direction.

17. The heat transfer pad of claim 16, wherein said first planar area is half of said overall planar area and said second planar area is half of said overall planar area.

18. The heat transfer pad of claim 16, wherein said heat transfer fluid outlet is positioned at said central longitudinal axis of said bladder.

19. The heat transfer pad of claim 16, wherein said volume of said first portion of said heat transfer fluid is equal to said volume of said second portion of said heat transfer fluid.

20. The heat transfer pad of claim 16, wherein essentially the entirety of said first flow channel occupies said first opposing side of said bladder and essentially the entirety of said second flow channel occupies said second opposing side of said bladder.

21. A heat transfer pad comprising:
a bladder having an internal flowpath for a flow stream of a heat transfer fluid, said bladder having a first side edge, a second side edge, a central longitudinal axis between said first side edge and said second side edge and an inlet chamber extending along said central longitudinal axis to an inlet chamber termination at a first flow opening and a second flow opening, both said first flow opening and said second flow opening in fluid communication with said inlet chamber,
wherein said inlet chamber has a first longitudinal sidewall and a second longitudinal sidewall enclosing opposing sides of said inlet chamber to enable flow of a heat transfer fluid therethrough in an inlet chamber direction,
wherein each of said longitudinal sidewalls is continuous and fluid-impermeable to prevent said heat transfer fluid from exiting said inlet chamber except at said first flow opening and said second flow opening,
wherein said inlet chamber bisects said bladder into a first half and a second half and divides said internal flowpath into a tortuous first flow channel at said first opening through which a first portion of said flow stream of said heat transfer fluid flows and a tortuous second flow channel at said second opening through which a second portion of said flow stream of said heat transfer fluid flows,
wherein each of said flow channels is in fluid isolation from the other along essentially the entirety of its length,
wherein said first flow channel occupies essentially the entirety of said first half of said bladder and said second flow channel occupies essentially the entirety of said second half of said bladder,
wherein said first flow channel has a first series of successive side-by-side switchback sections,
wherein said first series has a first side-by-side switchback section extending from said first flow opening and doubling back longitudinally alongside said inlet chamber in adjoining relationship thereto, thereby enabling flow of said heat transfer fluid through said first side-by-side switchback section of said first series in a first first series direction counter-current to said inlet chamber direction,
wherein said second flow channel has a second series of successive side-by-side switchback sections,
wherein said second series has a first side-by-side switchback section extending from said second flow opening and doubling back longitudinally alongside said inlet chamber in adjoining relationship thereto on a side of said inlet chamber opposite said first side-by-side switchback section of said first series, thereby enabling flow of said heat transfer fluid through said first side-by-side switchback section of said second series in a first second series direction counter-current to said inlet chamber direction and co-current to said first first series direction, wherein said first series of successive side-by-side switchback sections has a second side-by-side switchback section extending from said first side-by-side switchback section of said first series and doubling back longitudinally alongside said first side-by-side switchback section of said first series in adjoining relationship thereto and closer to said first side edge of said bladder, thereby enabling flow of said heat transfer fluid through said second side-by-side switchback section of said first series in a second first series direction co-current to said inlet chamber direction and counter-current to said first first series direction and said first second series direction, and wherein said second series of successive side-by-side switchback sections has a second side-by-side switchback section extending from said first side-by-side switchback section of said second series and doubling back longitudinally alongside said first side-by-side switchback section of said second series in adjoining relationship thereto and closer to said second side edge of said bladder, thereby enabling flow of said heat transfer fluid through said second side-by-side switchback section of said second series in a second second series direction counter-current to said first second series direction and said first first series direction and co-current to said inlet chamber direction and said second first series direction;

an inlet port into said bladder for feeding fresh heat transfer fluid to said inlet chamber; and an outlet port out of said bladder for discharging spent heat transfer fluid from said bladder.

22. The heat transfer pad of claim 21, wherein said bladder has a local heat transfer rate gradient centered at said central longitudinal axis and extending perpendicularly outward in opposing directions therefrom toward said first side edge of said bladder and toward said second side edge of said bladder and wherein local heat transfer rate of said bladder diminishes as said local heat transfer gradient extends away from said central longitudinal axis in opposing directions toward said first and second side edges.

23. The heat transfer pad of claim 21, wherein said bladder exhibits a highest local heat transfer rate at a central longitudinal region of said bladder containing said inlet chamber and said first switchback sections of said first and second series on opposing sides of said inlet chamber.

24. The heat transfer pad of claim 23, wherein said bladder exhibits a lower local heat transfer rate at a region of said bladder more proximal said first and second side edges of said bladder than said central longitudinal region.

* * * * *